United States Patent [19]
Ducos et al.

[11] Patent Number: 5,943,821
[45] Date of Patent: Aug. 31, 1999

[54] PROCESS FOR PACKAGING PLANT TISSUES CULTURED IN VITRO FOR TRANSPORT

[75] Inventors: Jean-Paul Ducos, Tours; Bruno Florin, St Cyr-sur-Loire; Vincent Petiard, Tours, all of France

[73] Assignee: Nestec S.A., Vevey, Switzerland

[21] Appl. No.: 08/881,057

[22] Filed: Jun. 24, 1997

[30] Foreign Application Priority Data

Jun. 25, 1996 [EP] European Pat. Off. ............ 962017638

[51] Int. Cl.⁶ ...................................................... C12N 5/00
[52] U.S. Cl. ........................... 47/58.1; 47/57.6; 435/420; 435/430; 435/430.1; 435/395; 435/398
[58] Field of Search .................................... 47/58.1, 57.6; 435/420, 430, 430.1, 395, 398

[56] References Cited

U.S. PATENT DOCUMENTS

| | | |
|---|---|---|
| 4,608,342 | 8/1986 | Nees et al. . |
| 4,615,141 | 10/1986 | Janick et al. . |
| 5,138,793 | 8/1992 | Florin et al. . |

FOREIGN PATENT DOCUMENTS

| | | |
|---|---|---|
| 0399158 | 11/1990 | European Pat. Off. . |
| 3818440A1 | 7/1989 | Germany . |
| 2185998A | 8/1987 | United Kingdom . |
| WO 82/1979 | 6/1982 | WIPO . |

OTHER PUBLICATIONS

Delvallse, et al., "Cryopreservation of Immature Maize Embryos After Freeze–Hardening in the Ear and In Vitro", Plant Science, 60, (1989) 129–136.

Chen, et al., "Cryopreservation of Alkaloid–Producing Cell Cultures of Periwinkle (*Calharanthus roseus*)", Plant Physiol., (1984) 75, 726–731.

Caplin, "Mineral Oil Overlay For Conservation of Plant Tissue Cultures", American Journal of Botany, vol. 46, pp. 324–329.

Derwent Information Ltd., Database Abstract WPI Accession No. 89–364815/198950, abstract of Mark, German Patent Application Publication No. DE 3 818 440 A1.

Agricell Report, Germplasm Exchange Using Alginate–Coated Nodal Segments of Yam, Jan. 1996.

*Primary Examiner*—Leon B. Lankford, Jr.
*Attorney, Agent, or Firm*—Vogt & O'Donnell, LLP

[57] ABSTRACT

Plant tissues which have been cultured in vitro are packaged with a nutritive medium for survival of the tissues in a sealed sterile container and with support members so that the plant tissues are positioned between surfaces of the support members. The support members have opposing surfaces for supporting the tissues and for support by a surface of the container and are made of a material suitable for being impregnated by the nutritive medium, and the container has a surface sized suitably for supporting the surface of the support member. At the time of packaging, at least one of the two support members is impregnated with the nutritive medium in an amount so that the tissues attach, by capillarity, to one surface of the at least one impregnated support member and so that the opposing surface of the at least one impregnated support member, when packaged, attaches, by capillarity, to the container surface.

25 Claims, 1 Drawing Sheet

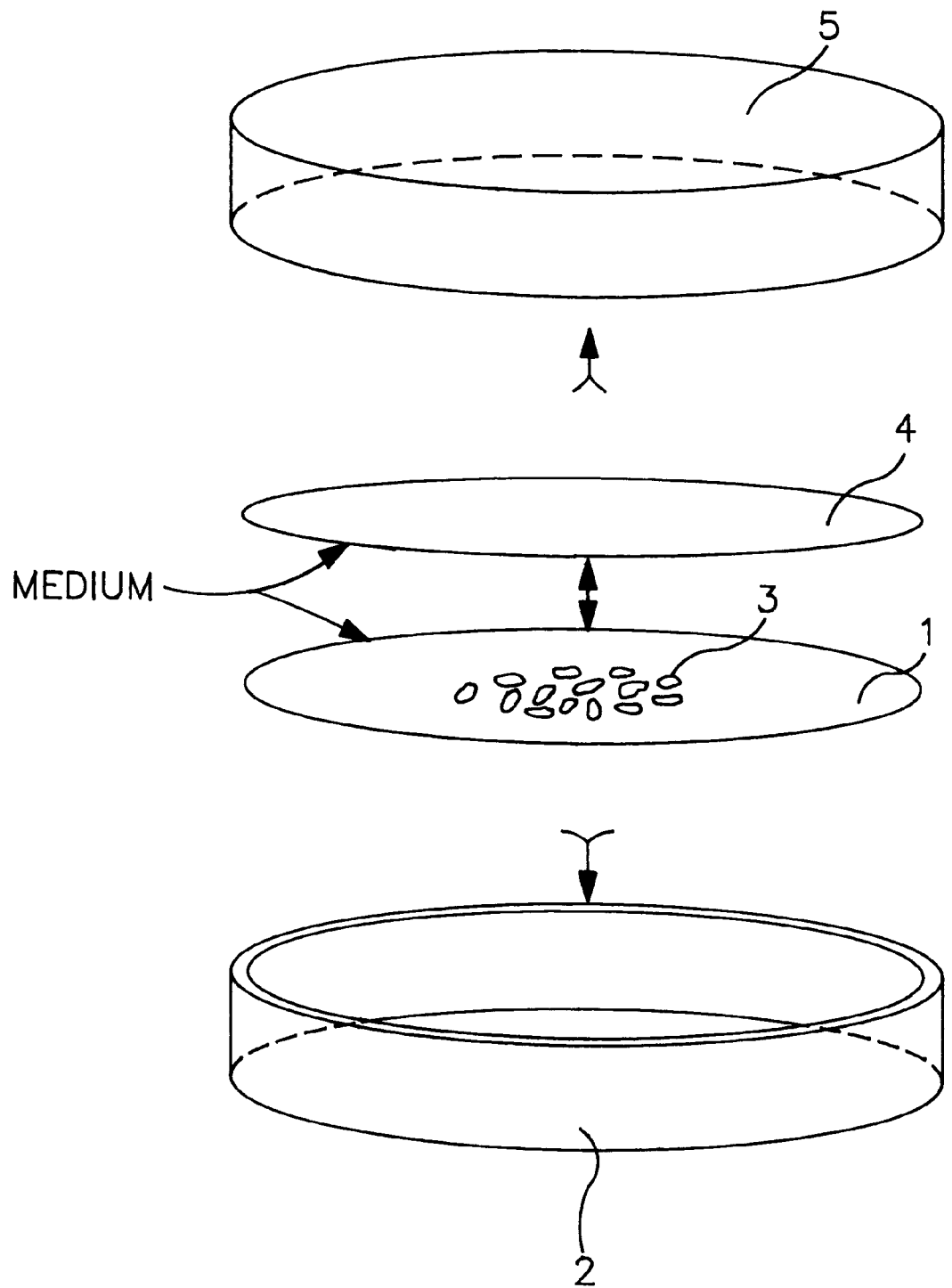

PROCESS FOR PACKAGING PLANT TISSUES CULTURED IN VITRO FOR TRANSPORT

BACKGROUND OF THE INVENTION

The present invention relates to packaging plant tissues cultured in vitro so that the tissues packages are preserved in the package, particularly for and during transport of the tissues.

The transport of plant tissues cultured in vitro requires an appropriate packaging. For example, plant tissues may be packaged by placing them in a liquid culture medium or on a semi-solid agar medium, these media being contained in customary containers for in vitro culture, such as Petri dishes or bottles. Unfortunately, this type of packaging does not correspond to the dangers to which a packet may be subjected during transport, namely, (1) asphyxiation of the tissues by a lack of agitation in the case of liquid cultures; (2) a covering of the tissues with agar due to excessive shakings which will cause asphyxiation of the tissues; (3) contaminations resulting from contact between the culture media and the outside of the containers; and (4) excessive growth of the tissues in the case of some species.

It is also possible to package plant tissues cultured in vitro under a layer of oil at refrigeration temperatures. European Patent Application Publication No. 0 408 922 describes a process in which embryos are kept in hypoxia by immersion under a layer of oil and are cooled and preserved at a temperature greater than the cold sensitivity threshold of the embryos considered. Although the embryos thus preserved exhibit a satisfactory viability after a few days of preservation, this method is still subject to the hazards of changes in refrigeration temperatures during transport.

It is also possible to transport plant tissues cultured in vitro when they are coated with a mixture of alginate and sucrose (Hasan et al., Plant Genetic Resources Newsletter, 103, 32–35, 1995).

It is also possible to freeze tissues of plants cultured in vitro. By way of example, Chen et al. propose culturing calli in the presence of sorbitol (dehydrating agent) and dimethyl sulphoxide (cryoprotectant), freezing them slowly at −40° C. and then in liquid nitrogen (Plant Physiol., 75, 726–731, 1984). Likewise, Delvallée et al. propose culturing immature zygotic embryos in the presence of sucrose (dehydrating agent) and dimethyl sulphoxide, and then freezing them in liquid nitrogen (Plant Science, 60, 129–136, 1989). Finally, European Patent Application Publication No. 0 399 158 describes a process in which somatic embryos are pretreated on a medium comprising an osmotic pressure agent, and then they are cooled and they are frozen at a temperature of between −15° C. and −40° C. Unfortunately, freezing is not always suited to the transport of plant tissues because of the temperature hazards which may lead to the death of the tissues.

Moreover, in a different technical field, methods for preserving plant cuttings or seeds are known. European Patent Application Publication No. 66 581 proposes, for example, a device for causing seeds to germinate or for preserving plant cuttings, which consists of a container in which the biological material is placed between a first adhesive support and a second supple support which can be impregnated with liquid components, both supports being kept firmly attached by the adhesive surface of the first support, and the two supports being kept on the sides of the container by means of adhesives. It may be noted that this device is not sterilizable because of the presence of adhesives. Furthermore, the adhesive surface of the first support is capable of damaging soft tissues, such as plant tissues cultured in vitro, which further limits the attraction of this device within the framework of the present invention.

So far, no device for packaging plant tissues cultured in vitro is therefore known which is both simple to use and which can satisfactorily protect the plant tissues.

SUMMARY OF THE INVENTION

The present invention provides a simple process for packaging plant tissues cultured in vitro which is particularly suited to the transport of somatic embryos and which requires only very little technical means and implementation time.

To this end, the invention provides a process for packaging plant tissues cultured in vitro in which, in a sterile container, plant tissues cultured in vitro are placed between the surfaces of two solid supports impregnated with liquid nutrient medium, the plant tissues being kept firmly attached to at least one of the surfaces of the supports by capillarity, at least one of the other surfaces of the supports also being kept firmly attached to one of the sides of the container by capillarity, and the tissues are preserved as they are.

The invention also relates to a packaging device comprising plant tissues cultured in vitro, the device consisting of a sealable sterile container in which plant tissues cultured in vitro are placed between the surfaces of two solid supports impregnated with liquid nutrient medium, the plant tissues being kept firmly attached to at least one of the surfaces of the supports by capillarity, at least one of the other surfaces of the supports also being kept firmly attached to one of the sides of the container by capillarity.

Although the prior art recommends techniques which are considerably more sophisticated, it has been observed that the plant tissues cultured in vitro survive perfectly under the packaging conditions according to the invention during a transport time which may range from 1 to 100 days. The present process thus avoids the disadvantages of the prior art because it is easy to implement, the risks of contamination are reduced, the tissues do not risk being completely immersed in nutrient medium, the tissues are protected from shocks by virtue of their insertion between the supports, and the tissues are very easily cultured after preservation because they simply have to be placed in a semi-solid agar or liquid nutrient medium, for example.

Surprisingly, it was observed that most of the slow-growing plant species, such as woody plants for example, have a growth which is reversibly inhibited by such packaging conditions. On the other hand, if it is desired to limit the growth of plant species having a more rapid growth, such as legumes, they can also be dehydrated before packaging them, for example.

Surprisingly, it was observed that the packaging conditions according to the invention could even enhance the capacity of somatic embryos to develop into a plantlet.

DETAILED DESCRIPTION OF THE INVENTION

To carry out the present invention, plant tissues derived from an in vitro culture, namely calli, buds which may have developed on a callus, somatic embryos and roots are used, for example. The invention is however preferably intended for the preservation of somatic plant embryos which are known to be particularly sensitive to their surroundings.

The container which is used may be any vessel which can be sterilized and which can be reversibly sealed, for example. A container known to persons skilled in the art and which is available in a large quantity is a Petri dish, which can be sealed by means of a plastic film, wax or another appropriate material known to persons skilled in the art, for example.

The solid supports used preferably consist of a supple material which may possibly, but not necessarily, take the shape of a mass of plant tissues, and which does not disintegrate over time. To this end, this material may be partially or completely fibrous and may include a material capable of retaining a liquid, the fibres also being capable of fulfilling this function, for example. These supports may thus consist, alone or in combination, of cellulose (blotting paper), silica, glass, polymers of dextran or of chitin, proteins such as silk, or synthetic polymers of the polystyrene, polyacrylate, polymethacrylate, polyvinyl and polyamide, such as nylon, types for example. Furthermore, the material retaining water and capable of being included in the fibers may consist of organic or inorganic compounds which absorb aqueous liquids to form a hydrogel, such as for example polyacrylamides or polysaccharides such as agar. However, this material should not be able to flow from the support.

The supports should be suitable for being impregnated with a liquid comprising the nutritive elements essential for the survival of the tissues. Among the nutrient media known to persons skilled in the art, there may be mentioned, by way of example, the Murashige and Skoog medium supplemented with vitamins from Skoog or Linsmayer (Physiol. Plant., 1962, vol. 15 p. 473; Physiol. Plant., 1965, vol. 18, p. 100)

Preferably, at least one of the supports may be impregnated with nutrient liquid up to the maximum water retention threshold of the support, after which it can no longer retain liquid. The quantity of liquid impregnated is preferably such that it ensures a relative humidity in the container of at least 95–100%, preferably at least 98%, for at least 1 to 5 days. The act of placing the plant tissues between a dry support and a second impregnated support makes it possible to obtain a slow controlled dehydration of the tissues, the dry support indeed becoming slowly impregnated with liquid which migrates from the impregnated support to the dry support.

It is advantageous to use supports of small thickness and weight so as not to damage the tissues and also to promote good diffusion of oxygen as well as adherence, by capillarity, of the supports to each other and to the surface of the container. By way of example, filters weighing 0.03 to 1 g, for example 0.03 to 0.1 g, and being capable of absorbing more than 2 to 10 times their initial weight of nutrient liquid, for example, may be used.

The plant tissues may be placed between the supports as a mass or individually without the viability of the tissues being affected thereby. Before placing the tissues, it is not necessary to separate the residual culture medium from the plant tissues taken from their culture medium, for example by vacuum suction through a filter. However, if it is desired to ensure a more pronounced dehydration of the tissues, as described above, the residual culture medium may also be separated.

Finally, 1 to 100 plant tissues cultured in vitro are placed per $cm^2$ of support, knowing that the tissues may be 0.05 to 1 cm long, and for example 0.05 to 0.3 cm long in the case of somatic embryos taken from the "torpedo" development stage.

It may be desirable to ensure that the supports are equally well kept firmly attached by capillarity. For that, there may be provided on the supports, at the periphery of the zone where the plant tissues are placed, a sufficiently wide circular zone around the tissues which is on the order of at least 1 cm and which will remain free of all tissues and which is intended to ensure good adherence of the supports to each other.

Finally, both supports, including the plant tissues cultured in vitro, are placed in the appropriate container, at least one of the supports being maintained attached to the container simply by capillarity from a surface of one of the supports to one of the surfaces of the container.

The present process may be applied to small-sized objects, and it allows an easy transport of large numbers and is therefore compatible with a commercial distribution. For example, if it is desired to distribute a large quantity of somatic embryos of a given plant species, it is possible to place, according to the present process, in standard Petri dishes 5.5 cm in diameter and 1 cm in height, about 100 embryos 0.05 to 0.2 cm in length. A 1 $m^3$ packet will thus contain 3,280 dishes, that is to say about 328,000 embryos, for example. For comparison, a transport of leafy plantlets with roots and a pair of leaves generally comprises 5,000 to 10,000 plantlets per $m^3$, for example.

The present process applies to all plant species, especially woody plants such as the coffee tree, the cacao tree, the hevea tree, the banana tree, the coconut tree and the oil palm tree, and especially legumes such as tomato, carrot, pea, celery and fennel. Persons skilled in the art have numerous techniques for obtaining plant tissues cultured in vitro and can even adapt them to each plant species, which may require special conditions as regards the obtaining of certain types of tissues, such as for example the embryos, buds or roots. As a guide, the somatic embryogenesis of the cacao tree, the coffee tree, the oil palm tree and of the carrot may be achieved according to the procedures described in U.S. Pat. No. 5,312,801, by Zamarripa (Café Cacao et Thé, 35, 233–244, 1991), by Engelmann et al. (Oléagineux, 41, 169–172, 1986) and in European Patent Application Publication No. 0 399 158, respectively.

The present process applies in particular to all plant species, especially the woody plants, having, in in vitro culture, a slow growth characterized by a multiplication rate of less than 10 per week, that is to say less than 10 times more fresh material each week, for example. As a guide, an embryo having a slow growth passes from a size of 1 mm to 10 mm in 1 to 2 months (the greatest length is considered), for example.

The slow-growing plant tissues are preserved during the transport time (1–100 days) preferably in the dark and/or at a temperature of 10C. to 35° C., in particular 15–30° C.

If the tissues have been dehydrated, it is also possible to preserve the tissues according to the invention in the dark and/or at refrigeration or even freezing temperatures (for example –4° C.) up to 30–35° C. However, care will be taken not to dehydrate tissues containing chlorophyll because such a treatment is then likely to irreversibly damage the tissues.

To dehydrate the tissues, besides or even in addition to the technique described above, it is for example sufficient to culture the tissues on a traditional culture medium, to which an osmotic pressure agent is added and to which certain organic substances, such as vitamin B1, nicotinic acid or adenine may also be added. The agent may be chosen by persons skilled in the art from substances capable of penetrating the tissues and ensuring an adequate osmotic pressure in order to obtain a satisfactory dehydration of the cell without influencing its membrane permeability. This agent may be a sugar such as sucrose or trehalose, or any other substance known to fulfil the same functions. The concentration of osmotic pressure agent in the culture medium is preferably not too low so as to ensure satisfactory dehydration of the cell. It should neither be too high so as not to damage the tissues or prevent them from growing again after preservation. As a guide, tissues may be dehydrated on a culture medium comprising 50 to 190 g/l of sucrose, in particular 100 to 150 g/l.

The dehydration of the tissues may also be a means for reversibly inhibiting the growth of the tissues when it appears that the process according to the invention is not sufficient to sufficiently inhibit the growth of the tissues. To this end, the tissues having a multiplication rate greater than 10 per week (10 times more fresh material) are preferably dehydrated as described above, for example. As a guide, an embryo having a rapid growth passes from a size of 1 mm to 10 mm in 4 to 6 days (the greatest length is considered), for example. Among the plants having a rapid growth in in vitro culture, there may be mentioned carrot, celery and fennel, for example.

After transport, the unpacking of the tissues is very easy since it is sufficient to shake the supports over a culture medium so as to detach the tissues therefrom. They can also be transplanted individually with instruments known to persons skilled in the art.

The invention is described in greater detail in the examples presented below and with reference to the accompany drawing FIGURE, and the characteristics of the process according to the invention are not limited to the specific examples described below, which may be adapted by persons skilled in the art to any plant species and tissues.

BRIEF DESCRIPTION OF DRAWING FIGURE

The drawing FIGURE illustrates the components of the present invention.

DETAILED DESCRIPTION OF THE DRAWING FIGURE

In the drawing FIGURE, as shown by the exploded perspective, support members 1 and 4 are depicted with a Petri dish 2 and its cover 5. As illustrated, the support members have opposing surfaces for supporting and containing therebetween the plant tissues and for support by the bottom surface of the container and as illustrated, plant tissues 3 are positioned on support member 1. The container dish has a bottom surface sized suitably for positioning and supporting the surfaces of the support member thereon. In accordance with the invention, the support 1 (filter made of glass fiber), impregnated with nutrient liquid, is reversibly attached by capillarity at the bottom of a Petri dish, the other surface of the support receiving the plant tissues 3 cultured in vitro. The second support 4 (filter made of glass fibre), which may be impregnated with nutrient liquid, comes into contact with the tissues 3 and with the first support 2. Finally, the cover 5 of the Petri dish makes it possible to close the container, it being possible to carry out a final sealing by means of a plastic film for example.

EXAMPLES

As indicated above, the following Examples further illustrate the present invention.

Example 1

100 somatic embryos of Robusta coffee tree (*Coffea canephora*), obtained at the torpedo stage according to the Zamarripa et al. procedure (Café Cacao et Thé, 35, 233–244, 1991), are placed, one by one, between two filters made of glass fiber (Whatman GFC, diameter 5 cm, 0.01 g of dry weight) impregnated with the Murashige and Skoog liquid culture medium. It can be noted that the impregnated filters do not release any liquid. The filters are placed in a Petri dish.

Several Petri dishes comprising coffee tree embryos are prepared in the same manner, they are preserved at 20° C. and then periodically the embryos are placed in a culture dish on a semi-solid medium, and the number of embryos surviving (viability) and the number of embryos capable of developing into a plantlet (conversion) are determined.

The results, presented in the table below, show that all the embryos survive perfectly at 15 days of preservation, and that the conversion to plantlets of embryos preserved for 1 to 30 days is much better than that of embryos taken at the torpedo stage and not having been subjected to packaging.

| Number of days | Viability (%) | Conversion (%) |
|---|---|---|
| 0 (control) | 97 ± 3 | 32 ± 4 |
| 15 | 100 | 71 ± 5 |
| 30 | 89 ± 11 | 52 ± 3 |
| 45 | 73 ± 13 | 34 ± 9 |
| 60 | 36 ± 31 | 12 ± 10 |

Example 2

1 g of somatic embryos of Robusta coffee tree (*Coffea canephora*), obtained at the torpedo stage according to the Zamarripa et al. procedure is placed, as a mass, between two glass filters (Whatman GFC, diameter 5 cm, 0.01 g of dry weight) impregnated with the Murashige and Skoog liquid culture medium. It can be noted that the impregnated filters do not release any liquid. The filters are then placed in a Petri dish. Several Petri dishes comprising coffee tree embryos are prepared in the same manner, they are preserved at 20° C. for 4 weeks and then 2,450 embryos are placed on a semi-solid medium, and the number of embryos capable of developing into a plantlet (conversion) is determined. The results show that 794 plantlets develop in 5 months. The embryos packaged therefore exhibit a conversion rate of 32%, which is similar to the conversion rates traditionally exhibited by non-packaged coffee embryos (see the table).

Example 3

In a manner similar to Example 2, 0.1 g of calli from Robusta coffee tree (*Coffea canephora*) is packaged per Petri dish, the calli are preserved for 1 month at 20° C., they are placed in culture on a semi-solid medium for 1 month, then the weight of the plant material thus obtained is determined (0.55±0.23 g of fresh material) and it is compared with the weight of plant material from a non-packaged control culture of 1 month which has been inoculated with 0.1 g of fresh calli (0.59±0.18 g of fresh material). The results thus show that the coffee tree calli-perfectly survive the packaging.

Example 4

Somatic embryos taken at the torpedo stage are pretreated on a medium comprising an osmotic pressure agent, as described in European Patent Application Publication No. 0 399 158, and then they are packaged as described in Example 2. The carrot embryos thus packaged for several days retain a viability and a capacity to develop into a plantlet which are comparable to non-packaged carrot embryos.

Example 5

Somatic carrot embryos taken from the torpedo stage are packaged as described in Example 2, the only difference being that the embryos are dehydrated beforehand on a medium comprising 100 g/l of sucrose, and then they are placed between a filter made of glass fibre impregnated with nutrient liquid and another dry filter. The carrot embryos thus packaged for several days retain a viability and a capacity to develop into a plantlet which are comparable to non-packaged carrot embryos.

We claim:

1. A process for providing packaged tissues which have been cultured in vitro which comprises packaging in a sterile container (i) plant tissues which have been cultured in vitro together with (ii) two support members and with (iii) a nutritive medium for survival of the tissue and sealing the container, wherein the support members comprise a material suitable for being impregnated with the nutritive medium for survival of the tissues and have opposing surfaces for supporting the tissues and for support by a surface of the container and wherein the container has a surface sized suitably for supporting the surface of a support member, and which comprises positioning the tissues between the surfaces of the two support members and in the container and wherein, at the time of packaging, at least one of the two support members is impregnated with the nutritive medium in an amount so that the tissues attach, by capillarity, to one surface of the at least one impregnated support member and in an amount and also packaging so that the opposing impregnated support member surface attaches, by capillarity, to the container support surface.

2. A process according to claim 1 wherein the support member material comprises a fibrous material.

3. A process according to claim 2 wherein the fibrous material comprises a substance selected from the group consisting of cellulose, silica, glass, a dextran polymer, a chitin polymer, a protein and a synthetic polymer.

4. A process according to claim 1 wherein the nutritive medium is in an amount so that the sealed container contains an atmosphere having a relative humidity of at least 95% for from 1 day to 5 days.

5. A process according to claim 1 wherein, at the time of packaging, one support member is not impregnated with the nutritive medium.

6. A process according to claim 5 wherein the support member not impregnated is dry.

7. A process according to claim 1 wherein each support member is impregnated with the nutritive medium.

8. A process according to claim 6 wherein the nutritive medium is in an amount so that the sealed container contains an atmosphere having a relative humidity of at least 95% for from 1 day to 5 days.

9. A process according to claim 1 wherein the tissues are selected from the group consisting of roots, calli and buds developed on a callus.

10. A process according to claim 1 wherein the tissues are somatic embryos.

11. A process according to claim 1 wherein the tissues are embryos which have a multiplication rate of less than 10 per week.

12. A process according to claim 1 or 5 wherein the tissues are dehydrated embryos.

13. A process according to claim 1 wherein the embryos are embryos which have a multiplication rate of more than 10 per week.

14. A process according to claim 12 wherein the embryos are embryos which have a multiplication rate of more than 10 per week.

15. A process according to claim 1 wherein the plant tissues are somatic embryos selected from the group consisting of coffee tree, cocoa tree, and oil palm tree somatic embryos.

16. A process according to claim 1 further comprising maintaining the packaged tissue at a temperature of from $-4°$ C. to $+35°$ C.

17. Packaged plant tissues comprising a sealed sterile container and contained within the container, (i) two support members, (ii) a nutritive medium suitable for survival of plant tissue and (iii) plant tissues which have been cultured in vitro, wherein the support members comprise a material suitable for being impregnated by the nutritive medium and comprise opposing surfaces suitable for supporting the tissues and for support by a surface of the container, wherein the container has a surface sized suitably for supporting the surface of a support member, wherein the support members and tissues are positioned so that the tissues are positioned between two of the support member surfaces and so that one of the support member surfaces is supported by the container surface and wherein at least one of the support members is impregnated with the nutritive medium so that the tissue is attached, by capillarity, to the at least one impregnated support member surface and so that the opposing impregnated support member surface is attached, by capillarity, to the container surface.

18. Packaged tissues according to claim 17 wherein the support member material comprises a fibrous material.

19. Packaged tissues according to claim 18 wherein the fibrous material comprises a substance selected from the group consisting of cellulose, silica, glass, a dextran polymer, a chitin polymer, a protein and a synthetic polymer.

20. Packaged tissues according to claim 17 wherein the nutritive medium is in an amount so that the sealed container contains an atmosphere having a relative humidity of at least 95% for from 1 day to 5 days.

21. Packaged tissues according to claim 17 wherein the tissues are selected from the group consisting of roots, calli and buds developed on a callus.

22. Packaged tissues according to claim 17 wherein the tissues are somatic embryos.

23. Packaged tissues according to claim 17 wherein the tissues are embryos which have a multiplication rate of less than 10 per week.

24. Packaged tissues according to claim 17 wherein the embryos are embryos which have a multiplication rate of more than 10 per week.

25. Packaged tissues according to claim 17 wherein the tissues are somatic embryos selected from the group consisting of coffee tree, cocoa tree and oil palm tree somatic embryos.

* * * * *